United States Patent [19]

Wullschleger

[11] Patent Number: 5,271,936
[45] Date of Patent: Dec. 21, 1993

[54] HEAT TREATMENT FOR DECREASING THE ALLERGENICITY OF PSYLLIUM SEED HUSK PRODUCTS

[75] Inventor: Richard D. Wullschleger, Battle Creek, Mich.

[73] Assignee: Kellogg Company, Battle Creek, Mich.

[21] Appl. No.: 826,745

[22] Filed: Jan. 28, 1992

[51] Int. Cl.$^5$ .................. C07H 1/00; A61K 35/00
[52] U.S. Cl. ...................... 424/195.1; 536/124; 536/128
[58] Field of Search .............. 536/1.1, 124, 128; 424/480, 195.1

[56] References Cited

U.S. PATENT DOCUMENTS

| | | | |
|---|---|---|---|
| 4,321,263 | 3/1982 | Powell et al. | 424/195.1 |
| 4,459,280 | 7/1984 | Colliopoulos et al. | 424/493 |
| 4,548,806 | 10/1985 | Colliopoulos et al. | 424/440 |
| 4,766,004 | 8/1988 | Moskowitz | 426/658 |
| 4,813,613 | 3/1989 | Salete | 241/7 |
| 4,828,842 | 5/1989 | Furst et al. | 424/480 |
| 4,911,889 | 3/1990 | Leland et al. | 422/26 |
| 5,085,785 | 2/1992 | Reeves | 210/767 |

FOREIGN PATENT DOCUMENTS 0105195 8/1983 European Pat. Off.

OTHER PUBLICATIONS

"A Closer Look at Dietary Fiber", Food Engineering, May 1985.
Chan et al. "A Forgotten Natural Dietary Fiber: Psyllium Mucilloid", Cereal Foods World, Nov. 1988, vol. 33, No. 11.

Primary Examiner—Johnnie R. Brown
Assistant Examiner—Elli Peselev
Attorney, Agent, or Firm—Felfe & Lynch

[57] ABSTRACT

Disclosed is a method of reducing the allergenicity of psyllium seed husks and psyllium seed husk-containing food additives. The method comprises subjecting ground psyllium seed husks to a wet heat treatment for a time and at a temperature and pressure sufficient to reduce the allergenicity of the psyllium seed husks. Psyllium seed husks alone can be subjected to the wet heat treatment to reduce its allergenicity and subsequently used as an ingredient to produce a psyllium-containing food additive or food product. Alternatively, psyllium seed husks can be mixed with one or more other ingredients of a food additive or food product and then subjected to the wet heat treatment during production of the food additive or food product.

10 Claims, No Drawings

HEAT TREATMENT FOR DECREASING THE ALLERGENICITY OF PSYLLIUM SEED HUSK PRODUCTS

BACKGROUND OF THE INVENTION

1. Field of the Invention

The present invention relates to a novel method for decreasing the allergenicity of psyllium seed husk and food products containing psyllium seed husk.

2. Discussion of the Background

Psyllium is a known mucilaginous material which has been used extensively in bulk laxatives. More recently, psyllium has been found to have a hypocholesterolemic effect if ingested by humans and lower animals.

The source of psyllium is the seeds from the plants of the Plantago genus, which grows in certain sub-tropical regions. The seeds are dark brown, smooth, boat-shaped and shiny. Since it is believed by those skilled in the art that the active ingredient of psyllium is the psyllium seed gum, which is located primarily in the seed husk, present technology uses the ground seed husk as the source for psyllium.

Generally, integral psyllium seeds are coarsely ground with crude grinding equipment in India and sub-tropical regions where the psyllium seeds originate in an attempt to separate the outermost husk material from the underlying pigmented seed coat layer of the psyllium seeds. In this crude grinding process, particles of various size from these layers are mixed with one another as a function of the grinding process. Because of the type and condition of the grinding equipment and variability in the physical dimensions of the psyllium seeds themselves, it is common to have discreet pieces of the seed coat mixed in with the husk material.

Various methods and apparatus for obtaining high purity mucilage or husk material from psyllium seeds have been proposed. For example, U.S. Pat. No. 4,813,613 discloses complex apparatus for producing powdered psyllium seed husk including a plurality of impact grinding steps.

Psyllium compositions have been incorporated into food products for many years (J. K. C. Chan, V. Wypyszyk, Cereal Foods World, 1988, 33: 919-922). Such food products include cookie compositions containing flours, sugars, oils, etc, baked goods, particularly muffins, psyllium containing dietary aids, and ready-to-eat cereal.

Exposure to psyllium seed husk powder can cause IgE sensitization and IgE-mediated allergic reactions in sensitized individuals (J. D. Bardy, J. L. Malo, P. Seguin, Am. Rev. Respir. Dis., 1987, 135:1033-1038). Most allergic reactions occur following ingestion of psyllium products, in particular, psyllium-containing bulk laxatives (J. S. Seggev, K. Ohta, W. R. Tipton, Ann. Allergy, 1984, 43:325-326).

A psyllium seed comprises a substantially centrally locate germ, an endosperm surrounding the germ, a relatively thin colored seed coat (bran) surrounding the endosperm, and a husk surrounding the colored seed coat. It has now been discovered that the seed coat material from psyllium seeds, in general, is high in protein content and specific protein fractions which contain allergens. As noted above, it is common to have discreet pieces of the seed coat material mixed in with coarsely ground psyllium seed husk. The present invention provides a novel, convenient and simple method for removing the allergen-containing specific protein fractions from coarsely ground psyllium seed husk to decrease the allergenicity of the psyllium seed husk. The method of the present invention provides a means for decreasing the allergenicity of psyllium seed husk without requiring size reduction of the coarsely ground psyllium seed husk or physical separation of the coarsely ground psyllium seed husk into fractions of different particle size.

SUMMARY OF THE INVENTION

The present invention provides a method for decreasing the allergenicity of psyllium seed husk and a food additive or a food product containing ground psyllium seed husk.

The present invention provides a method for reducing the allergen-containing specific protein fractions of psyllium seeds from psyllium seed husk in which ground psyllium seed husk is subjected to a wet heat treatment under predetermined temperature and moisture conditions to produce a psyllium seed husk having reduced allergenicity.

DESCRIPTION OF PREFERRED EMBODIMENT

The method of the invention alters the allergen-containing specific protein fractions of psyllium seeds, particularly psyllium seed coat material, found in psyllium seed husk. The method of decreasing the allergenicity of psyllium seed husk in accordance with the present method comprises subjecting psyllium seed husks to a wet heat treatment under predetermined temperature and moisture conditions for a time and at a pressure sufficient to alter allergen-containing specific protein fractions of psyllium seed material in ground psyllium seed husks.

In accordance with the present invention, ground psyllium seed husk itself can be subjected to the wet heat treatment or a mixture of ground psyllium seed husk with one or more food additive or food product ingredients can be subjected to the wet heat treatment.

Psyllium husk compositions typically contain many complex biochemical components in the husk, seed coat, etc., which are present in the psyllium composition. Surprisingly, the present method allows one to substantially reduce the allergenicity of these psyllium compositions without generating toxic decomposition products. Further, the present process allows one to reduce allergenicity and yet retain the food additive or food product qualities of the psyllium husk composition.

The allergenicity of psyllium seed husk treated by the process of the present invention can be determined by methods known in the art. As noted above, specific proteins in the psyllium seed are allergens. The allergenicity of the treated psyllium product can be determined by extracting protein from the treated psyllium product and then determining the allergenicity of the extracted proteins by known electrophoresis and immunoblotting techniques (H. A. Sampson and S. K. Cooke, J. Am. Coll. Nutrition, 9(4):410-17, John Wiley & Sons, Inc. (1990)). Immunoblotting allows one to determine the extent of IgE antibody binding to specific psyllium proteins, providing a measure of the allergenicity of psyllium protein fractions. One skilled in the art can readily utilize these known techniques to evaluate specific treatment conditions to determine adequate temperature, time and pressure to achieve the desired reduction in allergenicity.

According to one embodiment of the present invention, the method comprises mixing ground psyllium seed husks with water to provide a psyllium seed husk/water mixture containing from 20 to 99 weight percent water, based on the total weight of the psyllium seed husk/water mixture; heating the psyllium seed husk/water mixture at a temperature of from 210° to 275° F. for a time of 15 to 180 minutes at a pressure of 0 to 30 psi; and then optionally drying the psyllium seed husk to reduce the moisture of the psyllium seed husk to 14 percent or less to produce psyllium seed husk having reduced allergenicity. The reduced allergenicity psyllium seed husk can then be incorporated into a food additive or food product, as desired.

In another embodiment of the present invention, the method comprises mixing coarsely ground psyllium seed husk with one or more food additive or food product ingredients to form a psyllium seed husk/food ingredient mixture; mixing the psyllium seed husk/food ingredient mixture with water to produce a psyllium seed husk/food ingredient/water mixture having a water content of 20 to 50 weight percent and/or excess water, based on the total weight of the psyllium seed husk/food ingredient/water mixture; and then heating the psyllium seed husk/food ingredient/water mixture at a temperature of from 210° to 275° F. for a time of 15 to 180 minutes at a pressure of 0 to 30 psi to produce a psyllium seed husk-containing food additive or food product having decreased allergenicity.

In the first embodiment, the method of the present invention comprises subjecting ground psyllium seed husk to a wet heat treatment for a time and under moisture, temperature and pressure conditions sufficient to alter allergen-containing protein fractions of psyllium seed coat material in the ground psyllium seed husk. After being subjected to the wet heat treatment in accordance with this first embodiment of the invention, the psyllium seed husk exhibits significantly decreased allergenicity and is suitable for use as a food additive or as a psyllium nugget ingredient of a food additive or food product.

According to this embodiment of the invention, ground psyllium seed husk is mixed with water in a weight ratio of psyllium seed husk/water of from about 3:1 to about 1:99 to produce a psyllium seed husk/water mixture having a moisture content of about 20 to about 99%. If the moisture content of the psyllium seed husk/water mixture is below about 20%, the allergen-containing protein fractions may not be sufficiently altered to reduce allergenicity of the psyllium seed husk.

Preferably, the psyllium seed husk/water ratio is between about 3:1 and about 2:1 to provide a psyllium seed husk/water mixture having a moisture content of from about 25 to about 35%. Most preferably, the psyllium seed husk/water weight ratio is about 3:1 and the moisture content of the psyllium seed husk/water mixture is about 30%.

The psyllium seed husk/water mixture is then processed at a temperature between about 210° and about 275° F., preferably between about 245° to 265° F., at a pressure between 0 and about 30 psi, preferably about 14 to 20 psi, for a time period of about 10 to about 180 minutes, preferably about 15 to about 90 minutes. If the psyllium seed husk/water mixture is processed at a lower temperature, more time is required and if it is processed at a higher temperature less time is required. Processing times at these temperatures longer than about 180 minutes are not economical. If the processing time at these temperatures is shorter than about 10 minutes, the processing may be ineffective to alter the allergen-containing protein fractions.

It is especially preferred that the psyllium seed husk/water mixture is processed at a temperature between about 245° and about 255° F., most preferably at about 255° F. for about 45 to about 85 minutes, most preferably about 65 minutes at 255° F. (17 psi).

Conventional processing of foodstuffs with a heated extruder, for example in the preparation of cereal products, is insufficient to reduce the allergenicity of psyllium seed husk contained in the foodstuff material. Although cereal products are conventionally made using a heated extruder which may have a temperature above 200° F. and the extruded cereal may contain substantial amounts water, the residence time of the cereal in the extruder is insufficient to reduce the allergenicity of an extruded product containing psyllium seed husk. In contrast to conventional extruder processing, the wet heat treatment of the present invention is conducted for a time sufficient to substantially reduce the allergenicity of the psyllium seed husk, generally at least about 10 minutes.

In this invention, the three primary factors are heat, moisture and time. The moisture level must be 20 percent or higher. The presence of water in the psyllium seed husk material being processed retards burning or scorching which could render the psyllium seed husk unsuitable for consumption as a ingredient of a food product. Water also serves as an energy transport system.

Heat and time are inversely proportional in the present method. At high temperature, the time required to alter the allergen-containing protein fractions, and thereby reduce the allergenicity of the psyllium seed husk, is reduced. At lower temperatures, more time is required. The limits of the time/temperature/moisture relationship have been explored and the preferred ranges of each of these process parameters have been determined to be those set forth above. Limited moisture, excessive temperature or overexposure (time) can result in a burnt psyllium seed husk product which is not palatable or nutritional. The lipid constituents of the psyllium seed husk material remain substantially unaltered by the practice of the invention.

After the psyllium seed husk/water mixture has been processed as described above, the psyllium seed husk has a substantially decreased allergenicity. The processed psyllium seed husk/water mixture is then dried to a moisture content, preferably less than about 14%, for storage stability, preferably in a forced air oven or other suitable drying accelerating apparatus. Any conventional drying means may be employed to reduce the moisture content of the psyllium seed husk/water mixture to the desired level.

The dried psyllium seed husk, which exhibits significantly decreased allergenicity as compared to the initial ground psyllium seed husk, is then ready for use for any known purpose of psyllium seed husk, and is especially useful as an ingredient of a food additive and/or food product. The dried psyllium seed husk treated to reduce allergenicity according to the present invention has an allergenicity which is reduced by 30-100% relative to untreated dried psyllium seed husk. Preferably, the treated psyllium seed husk has an allergenicity which has been reduced by 60-100%, most preferably 90-100%, relative to the untreated product.

The dried psyllium seed husk of the present invention may be ground or powdered using conventional means to produce a free flowing powdered psyllium seed husk composition having reduced allergenicity. This free flowing powder may be used as a bulk laxative in solid form or may be dispersed in water or an aqueous beverage. The powdered psyllium has poor wetting capability, however, and must be vigorously mixed with aqueous fluids to produce a palatable dispersion. Accordingly, it is preferable to mix the dried psyllium powder with additives which promote dispersion of the psyllium powder in water or aqueous beverages. Suitable dispersion additives include sweeteners such as dextrose, as well as compositions for coating the psyllium seed powder to prepare formulations which are more easily dispersed in water or aqueous beverages. For example, improved dispersability is obtained when the psyllium seed powder is provided with a coating of a non-toxic water dispersable polymer and/or other materials by methods known in the art.

The free flowing psyllium seed husk powder of the present invention is substantially free of allergenicity caused by the presence of psyllium seed coat proteins. By "substantially free of allergenicity" as used herein, is meant a psyllium seed husk powder which does not contain proteins which are capable of binding to IgE antibodies which specifically bind antigenic psyllium seed coat proteins described in J. M. James et al, J. Allergy Clin. Immun., 88, (3):402–408 (1991).

According to another embodiment of the present invention, ground psyllium seed husk is mixed with one or more ingredients of a food additive or food product before the psyllium seed husk is subjected to the wet heat treatment of the inventive process. Examples of food additive ingredients and food product ingredients which can be mixed with the ground psyllium seed husk prior to the wet heat treatment of the psyllium seed husk include whole grains such as whole wheat, rice, oats, barley, corn and rye; grain components such as wheat germ and brans, including oat bran, wheat bran, etc.; flours such as wheat flour, corn flour, rice flour, graham flour, etc.; legumes such as soybeans, peas, beans and the like; non-bran fiber sources such as prune fiber, guar, beet fiber, and citrus pulp; and flavorings such as corn syrup, sucrose, sugar, malt syrup, salt, etc. Of course, this list of food additive or food product ingredients is merely exemplary and other known and novel food additive or food product ingredients may be added to ground psyllium seed husk prior to the wet heat treatment of the present invention.

Water is added to the ground psyllium seed husk and other food ingredient(s) to produce a psyllium seed husk-containing mixture having a moisture content of about 20 to about 50% and/or excess water, based on the total weight of the mixture. Preferably, the moisture content of the mixture is between about 25 and about 35%, and most preferably is about 30%.

The psyllium seed husk-containing mixture is then heated at a temperature of about 210° F. at 0 psi to about 275° F. at 30 psi for a time of from about 30 to about 180 minutes. Preferably, the psyllium seed husk-containing mixture is heated at a temperature of about 250° F. at 14 psi to about 260° F. at 20 psi, most preferably about 255° F. at 17 psi, for a time of between about 55 and about 75 minutes, most preferably about 65 minutes.

After heating, the psyllium seed husk-containing mixture is cooled and is suitable for use as a food additive or a final food product, depending upon the ingredients initially mixed with the ground psyllium seed husk. The treated psyllium seed husk-containing mixture has decreased allergenicity compared to a similar psyllium seed husk-containing mixture produced according to conventional processes wherein the psyllium seed husk is not subjected to the above-described wet heat treatment. The treated psyllium seed husk-containing mixture may be further processed as desired to produce a specific food product, such as a psyllium-containing ready-to-eat cereal or food additive. For example, the treated psyllium seed husk-containing mixture could be further processed in a variety of ways to produce a ready-to-eat psyllium-containing cereal of decreased allergenicity, depending upon the desired final shape of the ready-to-eat cereal pieces and the production steps and equipment used. The production steps and equipment for producing a ready-to-eat cereal in the form of biscuits, pellets, puffed products and flakes are all different, and are well known to those familiar with the ready-to-eat cereal making art.

The psyllium seed husk subjected to the wet heat treatment process in accordance with the present invention is preferably coarsely ground psyllium seed husk. Typically, commercially available coarsely ground psyllium seed husk will have a purity of about 70 wt %–about 95 wt %, preferably at least about 80 wt %. Obviously, the process of the present invention may be used to treat both impure coarsely ground psyllium seed husk, as well as more highly refined psyllium products having a purity of 85 wt %–98 wt % and even in excess of 99 wt % psyllium seed husk. Other features of the invention will become apparent in the course of the following description of an exemplary embodiment which is given for illustration o the invention and is not intended to be limiting thereof.

EXAMPLES

EXAMPLE 1

Psyllium seed husk of decreased allergenicity was produced as follows.

555 grams of coarsely ground psyllium seed husk having a purity of 85% was mixed with 693 grams of water to produce a psyllium seed husk/water mixture having a moisture content of 60%. The psyllium seed husk/water mixture was processed in an autoclave for 80 minutes, at a temperature of 260° F. at 20 psi. The wet heat processed psyllium seed husk mixture was then dried in a forced air oven for about 16 hours at a temperature of 113° F. to reduce the moisture content of the wet heat processed psyllium seed husk mixture to 12% or less.

The original 85% purity ground psyllium seed husk and the dried, processed psyllium seed husk were evaluated for their allergy-evoking response or allergenicity on a scale of 0 to 3, 0 being the lowest allergenicity rating and 3 being the highest allergenicity rating. The ground psyllium seed husk of 85% purity had an initial allergenicity rating of 2. The wet heat processed, dried psyllium seed husk had an allergenicity rating of 0.

These results clearly demonstrate that psyllium seed husk of greatly reduced allergenicity is produced by the wet heat treatment method of the present invention.

EXAMPLE 2

Psyllium seed husk of decreased allergenicity was produced as follows.

252 grams of coarsely ground psyllium seed husk having a purity of 85% was mixed with 76.76 grams of water to produce a psyllium seed husk/water mixture having a moisture content of 31%. The psyllium seed husk/water mixture was processed in an autoclave for the times, at the temperatures and pressures, shown in the following Table. The wet heat processed psyllium seed husk mixture was then dried in a forced air oven to reduce the moisture content of the wet heat processed psyllium seed husk mixture to about 10%.

The allergy-evoking response or allergenicity for each of the tested combinations of time, temperature and pressure, are shown in the following Table, on the scale of 0 to 3 described in Example 1.

TABLE

| Time (Minutes) | Temperature °F. | Pressure (P.S.I.) | Allergenicity Value |
|---|---|---|---|
| None | None | None | 2 |
| 45 | 248 | 14 | 2 |
| 55 | 248 | 14 | 1 |
| 65 | 248 | 14 | 1/2 |
| 30 | 255 | 17 | 2 |
| 45 | 255 | 17 | 1/2 |
| 55 | 255 | 17 | 1/2 |
| 65 | 255 | 17 | 1/2 |
| 75 | 255 | 17 | 1/2 |
| 45 | 260 | 20 | 1/2 |
| 55 | 260 | 20 | 1/2 |
| 65 | 260 | 20 | 1/2 |

The results set forth in the Table clearly demonstrate that psyllium seed husk of greatly reduced allergenicity is produced by the wet heat treatment method of the present invention.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

What is claimed is:

1. A process for reducing the allergenicity of ground psyllium seed husk, consisting essentially of:
   a) mixing ground psyllium seed husk with water to form a mixture; and
   b) subjecting the mixture of step (a) to a wet heat treatment in an autoclave for a time period of from about 10 to about 180 minutes, at a temperature of from about 210° to about 275° F., and at a pressure of 0 to about 30 psi, thereby altering allergen-containing protein fractions in said ground psyllium seed husk to produce psyllium seed husk having reduced allergenicity relative to untreated psyllium seed husk.

2. Process of claim 1, wherein a food ingredient is added to the mixture of step (a).

3. The process of claim 1, further comprising drying said ground psyllium seed husk/water mixture to a moisture content of about 14% or less after the wet heat treatment.

4. The process of claim 1, wherein the wet heat treatment is conducted at a temperature of from about 245° to 265° F.

5. The process of claim 1, wherein the wet heat treatment is conducted at a pressure of from about 14 to 20 psi.

6. The process of claim 1, wherein the heat treatment is conducted for a time of from about 15 to 90 minutes.

7. The process of claim 1, wherein the treated psyllium seed husk has an allergenicity reduced by 60-100% relative to untreated psyllium seed husk.

8. The process of claim 1, wherein the treated psyllium seed husk has an allergenicity reduced by 9-100% relative to treated psyllium seed husk.

9. The process of claim 2, wherein said mixture of ground psyllium seed husk, food ingredient and water has a moisture content of at least 20%.

10. The process of claim 2, wherein said mixture is heated at a temperature of from about 25° to 260° F. at a pressure of about 14 to 20 psi for a time of about 55 to 75 minutes.

* * * * *

UNITED STATES PATENT AND TRADEMARK OFFICE
CERTIFICATE OF CORRECTION

PATENT NO. : 5,271,936
DATED : December 21, 1993
INVENTOR(S) : Richard D. Wullschleger It is certified that error appears in the above-indentified patent and that said Letters Patent is hereby corrected as shown below:

| Column | Line | |
|---|---|---|
| 8 | 32 | "9-100%" should read --90-100%-- |
| 8 | 38 | "25°" should read --250°-- |

Signed and Sealed this

Twentieth Day of September, 1994

Attest:

Attesting Officer

BRUCE LEHMAN

Commissioner of Patents and Trademarks